| United States Patent [19] | [11] | 4,073,456 |
|---|---|---|
| Karapita et al. | [45] | Feb. 14, 1978 |

[54] SUSPENSION SUPPORT

[75] Inventors: Alexander Donald Karapita, 44 Lyme Regis Cres, Scarborough, Ontario, Canada; James Douglas Orr, Toronto, both of Canada

[73] Assignee: Alex D. Karapita, Scarborough, Canada

[21] Appl. No.: 706,107

[22] Filed: July 14, 1976

[51] Int. Cl.² .................. B42F 13/00; A47B 1/06
[52] U.S. Cl. .................. 248/337; 108/67; 403/15; 403/104; 248/354 H; 248/125; 248/404; 248/412
[58] Field of Search .......... 248/333, 336, 337, 338, 248/334, 335, 122, 125, 404, 412, 354 H, 354 R, 355; 403/15, 104; 188/67

[56] References Cited

U.S. PATENT DOCUMENTS

| 874,836 | 12/1907 | Dodge et al. | 248/337 |
|---|---|---|---|
| 2,453,855 | 11/1948 | Oliver | 403/15 |
| 2,907,598 | 10/1959 | Hart | 248/355 |
| 2,938,699 | 5/1960 | Bellmann | 248/354 H |
| 3,048,360 | 8/1962 | Foley | 248/337 |
| 3,191,904 | 6/1965 | Karapita | 248/333 |
| 3,533,583 | 10/1970 | Azim | 248/125 |
| 3,807,574 | 4/1974 | Lanza | 248/125 |

FOREIGN PATENT DOCUMENTS

| 1,365,427 | 5/1964 | France | 248/404 |
|---|---|---|---|
| 337,535 | 11/1930 | United Kingdom | 248/412 |
| 1,018,085 | 1/1966 | United Kingdom | 248/125 |

*Primary Examiner*—Marion Parsons, Jr.

[57] ABSTRACT

A manual suspension support, in which a pair of tubes are telescoped using a vacuum source. A slidable piston in a cylinder is selectively brakable by manipulation of a handle which also carries a valve operable to vary the vacuum in the cylinder.

17 Claims, 3 Drawing Figures

U.S. Patent Feb. 14, 1978 4,073,456
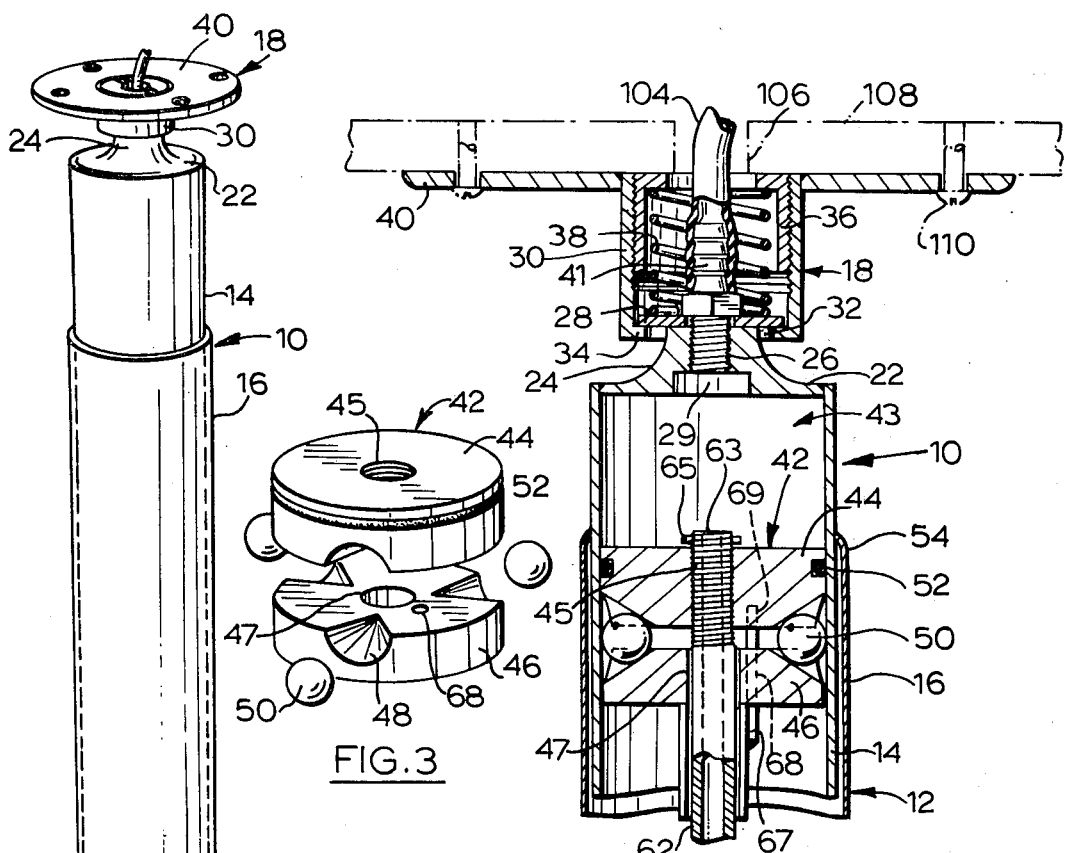
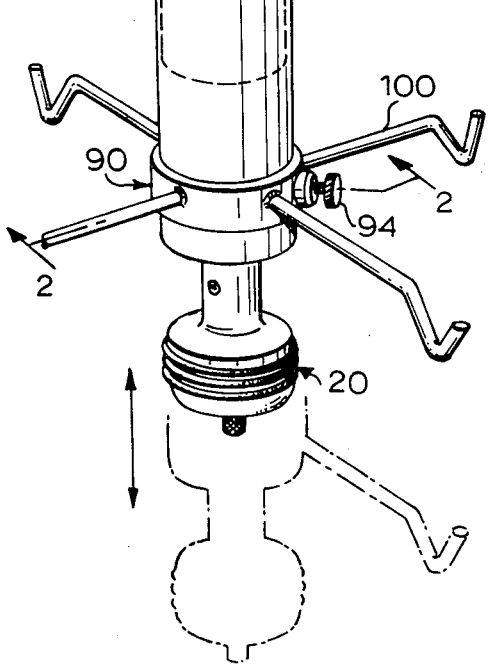
FIG.1
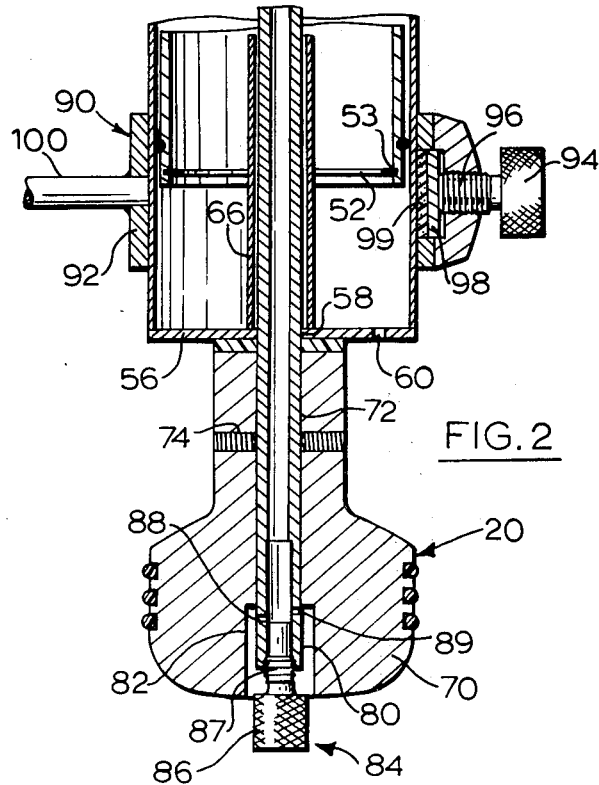

SUSPENSION SUPPORT

This invention relates to a vertically adjustable suspension support.

Adjustable suspension supports are used for example in hospitals where the support is suspended from the ceiling to carry plasma bottles for intravenous injections. An example of such a support is shown in U.S. Pat. No. 3,191,904 issued June 29, 1965 to A. D. Karapita. The combined weight of a plurality of such bottles makes it difficult to adjust the support upwardly, especially when operated by women nurses.

It is an object of the present invention to provide an improved suspension support which uses vacuum means to extend or retract the support and to maintain the support at any selected height.

Essentially the invention consists of a suspension support comprising a vertical cylinder having an upper end closure with a port therein connectable to a vacuum source, a piston slidable in the cylinder and forming, with the upper end closure, a closed chamber, means selectively actuable to brake the piston within the cylinder, valve means selectively operable to vent the chamber any degree, a handle positioned outside the cylinder and connected to the piston, means on the handle constructed and arranged to support an object, and means on the upper end of the cylinder to mount the support.

An example embodiment of the invention is shown in the accompanying drawings in which:

FIG. 1 is a perspective view of a suspension support;
FIG. 2 is a cross-sectional view taken along line 2—2 of FIG. 1; and
FIG. 3 is a perspective view of the piston shown in FIG. 2.

The example embodiment consists of suspension support 10 having a pair of vertical telescopic tubes comprising an inner cylinder 14 and an outer sleeve 16 coaxial with the cylinder, a socket mount 18 connected to the inner cylinder, and a handle 20 connected to the cylinder.

Inner cylinder 14 is closed at its upper end by an end plate 22 having an outwardly projecting boss 24 with a threaded central aperture 26 and an annular cap 28. End plate 22 has an inwardly facing recess 29.

Socket mount 18 comprises a cylindrical member 30 having a restrictive aperture 32 at one end forming an annular flange 34 and threaded at the other end to receive a flanged concentric insert 36. Boss 24 of inner cylinder 14 projects through aperture 32 into member 30 and cap 28 rests against flange 36. A compression spring 38 bears at one end against the flange of insert 36 and at the other end against flange 34 of members 30. A circular mounting flange 40 is fixed to member 30 remote from aperture 32. Member 30 houses a nipple 41 threaded into aperture 26 of end plate 22 to form a port.

A slidable piston 42 is located in inner cylinder 14 forming, with end plate 22, a closed chamber 43. Piston 42 comprises an upper disc 44 having a threaded central aperture 45 and a lower disc 46 having a central aperture 47. A plurality of conical sockets 48 extend inwardly from the periphery of piston 42 in the boundary between upper and lower discs 44 and 46, as seen more specifically in FIG. 3 of the drawings. Friction means in the form of spherical balls 50 are located in each socket 48. If desired, sockets 48 could be replaced by a raceway. Upper disc 44 carries an O-ring seal 52. The lower end of cylinder 14 carries an inwardly projecting stop ring 52 which rests in a groove 53 in the cylinder.

Outer sleeve 16 is turned inwardly at its upper end to form a flange 54 which is in frictional contact with inner cylinder 14. An end cap 56 closes the lower end of outer sleeve 16. End cap 56 has a central aperture 58 and an offset aperture 60.

Handle 20 is connected to piston 42 by a tubular rod 62 passing freely through aperture 47 of lower disc 46 with an upper threaded end 63 engaging threaded aperture 45 of upper disc 44. Upper end 63 of rod 62 projects from upper disc 44 of piston 42 and carries laterally projecting retaining pin 65. Upper end 63 of rod 62, together with retaining pin 65, are receivable in recess 29 of end plate 22. Spacer means comprising a tube 66 concentric about rod 62 bears at its lower end against end cap 56 of outer sleeve 16 and at its upper end against lower disc 46 of piston 42. A vertical pin 67 fixed tangentially to the upper end of tube 66 projects through an aperture 68 in lower disc 46 and into a recess 69 in upper disc 44. Handle 20 comprises a grip member 70 with a central bore 72 which receives the lower end portion of rod 62. Set screws 74 hold grip member 70 on rod 62 and in abutting relationship with end cap 56 of outer sleeve 16. Thus piston 42, outer sleeve 16, and handle 20 are movable vertically as a unit with respect to cylinder 14. Also handle 20 is rotatable with respect to piston 42, sleeve 16, and cylinder 14.

The lower end of rod 62 terminates in a recess 82 in the bottom of grip member 70 and is internally threaded to receive a valve 84 which consists of a knurled cap 86 and a threaded valve stem 87. A pair of apertures 88 and 89 are located in the wall of rod 62 adjacent the free end of valve stem 87 and the two apertures are offset one from the other longitudinally with respect to the axis of the rod.

The illustrated embodiment shows its use with means to support an object. The support means consists of a hanger 90 which comprises a collar 92 slidably mounted on outer sleeve 16 of support 10 and releasably secured on the support by a screw clamp 94. A threaded shank 96 of clamp 94 bears against a loose washer 98 which in turn bears against a loose pad of frictioned material 99 lying against outer sleeve 16. Collar 92 carries a plurality of fixed radial arms 100 each terminating at its free ends in a hook 102.

To mount the example device for operation, support 10 is coupled with a flexible vacuum outlet tube 104 shown projecting through an aperture 106 in a ceiling 108. To effect this coupling, mounting flange 40 is fixed to ceiling 108 by screws 110 concentric with aperture 106 and outlet tube 104 is attached to nipple 41 as seen in FIG. 2.

In the operation of the example embodiment, cylinder 14 and sleeve 16 are locked together by rotating handle 20 in a direction to draw piston discs 44 and 46 together. Pin 67 prevents the discs of piston 42 from rotating while rod 62 is being rotated. As discs 44 and 46 are drawn together they force balls 50 radially outwards to bear against the wall of cylinder 14 and the friction of the balls against the cylinder wall prevents vertical movement of sleeve 16 and also prevents piston 42 from rotating, although sleeve 16 is able to rotate about its axis. Also, valve 84 is rotated to close apertures 88 and 89 which allows outlet 104 to create a vacuum in chamber 43 and assists piston 42 in preventing downward movement of sleeve 16 and handle 20.

To lower hanger 90, as shown in broken lines in FIG. 1, support 10 is extended by releasing piston 42 in cylinder 14 and also allowing air to enter chamber 43 of the cylinder to neutralize the vacuum in the chamber whereupon piston 42, handle 20 and sleeve 16 drop as a unit by their own weight. Piston 42 is released by rotating handle 20 to separate discs 44 and 46, and air is allowed to enter chamber 43 by rotating valve 84 to open apertures 88 and 89. Recess 82 in grip member 70, together with valve cap 86, muffles the sound made by the air escaping through apertures 88 and 89. When the desired extended or lowered position has been reached, handle 20 is rotated in the opposite direction to draw piston discs 44 and 46 together as described above thus locking piston 42 against cylinder 14. Alternatively, or in conjunction therewith, valve 84 is rotated to close partially apertures 88 and 89 to reinstate the vacuum in chamber 43 to the amount necesary to hold piston 42 at the desired height To telescope support 10 and raise hanger 90, handle 20 is rotated to release piston 42 in cylinder 14. Apertures 88 and 89 remain closed by valve 84 which allows the vacuum in chamber 43 to raise piston 42, handle 20 and sleeve 16. When hanger 90 has been raised to its desired height, handle 20 is rotated in the opposite direction to lock position 42 against cylinder 14 as before.

It will be appreciated that outer sleeve 16 is merely a mount for hanger 90 and it could be suitably modified in accordance with the structure of hanger 90; for instance it could be shortened if the hanger were to be fixed in the position shown in the drawings.

We claim:

1. A suspension support comprising:
   a vertical cylinder having an upper end closure with a port therein connectable to a vacuum source;
   a piston slidable in the cylinder and forming, with the upper end closure, a closed chamber;
   means selectively actuable to brake the piston within the cylinder;
   valve means selectively operable to vent the chamber;
   a handle positioned outside the cylinder and connected to the piston;
   means connected with the handle to support an object; and
   means on the upper end of the cylinder to mount the support.

2. A support as claimed in claim 1 in which the piston comprises a pair of parallel discs and the brake means comprises friction means located between the discs and movable, on moving the discs one towards the other, radially outwards to contact the cylinder.

3. A support as claimed in claim 2 in which the handle means comprises a grip member engaging a rod axially rotatable to move the discs selectively towards and away one from the other.

4. A support as claimed in claim 3 in which the rod is threaded into the upper one of the pair of discs and freely slidable in the lower disc, and means to restrain the lower disc against downward movement with respect to the piston.

5. A support as claimed in claim 4 in which the discs are recessed to form a plurality of outwardly opening conical sockets therebetween, and the friction means comprises a plurality of spherical balls one in each socket.

6. A support as claimed in claim 3 in which the rod is tubular and forms a passage opening into the chamber, and the valve means comprises a valve operable to open and close the passage.

7. A support as claimed in claim 6 in which the grip member is concentric with the rod and the valve is coaxial with the rod.

8. A support as claimed in claim 7 in which the valve is recessed in the grip member.

9. A support as claimed in claim 3 in which the rod is threaded into the upper one of the pair of discs and freely slidable in the lower disc, a lower end closure on the sleeve abutting the handle, and a tube concentric with the rod, one end of the tube bearing against the lower disc and the other end of the tube bearing against the lower end closure of the sleeve in opposed relationship to the handle.

10. A support as claimed in claim 9 in which the lower disc has an aperture therethrough and the upper disc has a recess aligned with the aperture in the lower disc, a pin fixed on the upper end portion of the tube and upwardly extending therefrom through the aperture in the lower disc and engaging the recess in the upper disc.

11. A support as claimed in claim 1 in which the mounting means comprises a socket having a mounting flange fixed thereon, the upper end closure of the cylinder having a boss projecting upwardly into the socket, means on the boss to engage the socket internally, and compression spring means retained in the socket to urge the engaging means against the socket.

12. A support as claimed in claim 1 in which the support means comprises an outer sleeve concentric with the cylinder and slidable thereon, the sleeve being mounted on the handle, and means projecting outwardly from the sleeve to support an object, the projecting means being slidable along the sleeve.

13. A support as claimed in claim 12 in which the support means comprises a hanger having a collar slidable on the outer sleeve, a plurality of arms projecting radially from the collar, and means to clamp the collar releasably on the sleeve.

14. A suspension support comprising:
   a vertical inner cylinder having an upper end closure with a port therein connectable to a vacuum source;
   a piston slidable in the cylinder and forming, with the upper end closure, a closed chamber, the piston comprising a pair of parallel discs having means therebetween movable, on moving the discs towards each other, radially outwards to engage the cylinder frictionally to brake the piston;
   a rotatable tubular rod threaded into the upper one of said discs and having the passage thereof in communication with the closed chamber, the lower one of said discs being freely slidable on the rod, the rod projecting downwardly from the cylinder;
   an outer sleeve slidably mounted coaxially on the cylinder, the sleeve having a lower end closure and the rod projecting downwardly therethrough, spacer means bearing at one end against the lower disc and the other end against the lower end closure of the sleeve;
   handle means fixed to the lower end of the rod and bearing against the lower end closure of the sleeve in opposed relationship to the tube;
   valve means located in the passage of the rod at the lower end thereof and selectively operable to vent the chamber;
   means on the sleeve constructed and arranged to support an object; and means on the upper end of the cylinder to mount the support.

15. A support as claimed in claim 14 in which the spacer means comprises a tube concentric with the rod.

16. A support as claimed in claim 14 in which the support means comprises a hanger having a collar slidable on the outer sleeve, a plurality of arms projecting radially from the collar, and means to clamp the collar releasably on the sleeve.

17. A suspension support as claimed in claim 14 in which the means to mount the support comprises a socket having a housing with a flange defining a downwardly opening aperture, a cap mounted on the upper end of the cylinder and located in the housing, a compression spring bearing at one end against the housing and at the other end against the cap to urge the cap against the flange.

* * * * *